US007922211B2

(12) United States Patent
Årthun et al.

(10) Patent No.: US 7,922,211 B2
(45) Date of Patent: Apr. 12, 2011

(54) METHOD AND DEVICE FOR INTERCONNECTING, SEALED AGAINST CONTAMINATION, THE ENDS OF ELONGATE ELEMENTS SUCH AS TUBES OR PIPES

(75) Inventors: Nils Årthun, Sandnes (NO); Sten Johansson, Hisings Kärra (SE); Lennart Myhrberg, Älvängen (SE); Håkan Samuelsson, Onsala (SE)

(73) Assignee: Millipore AB, Solna (SE)

( * ) Notice: Subject to any disclaimer, the term of this patent is extended or adjusted under 35 U.S.C. 154(b) by 570 days.

(21) Appl. No.: 11/885,553

(22) PCT Filed: Feb. 8, 2006

(86) PCT No.: PCT/SE2006/000170
§ 371 (c)(1),
(2), (4) Date: May 5, 2008

(87) PCT Pub. No.: WO2006/093451
PCT Pub. Date: Sep. 8, 2006

(65) Prior Publication Data
US 2008/0217915 A1    Sep. 11, 2008

(30) Foreign Application Priority Data
Mar. 4, 2005    (SE) .................................... 0500494

(51) Int. Cl.
*F16L 35/00*    (2006.01)
(52) U.S. Cl. ............. 285/67; 285/68; 604/905; 604/533
(58) Field of Classification Search ................ 285/4, 67, 285/68, 71; 604/905, 533
See application file for complete search history.

(56) References Cited

U.S. PATENT DOCUMENTS

| 3,865,411 A | | 2/1975 | Rowe et al. |
| 3,900,223 A | * | 8/1975 | Schafer et al. ..................... 285/4 |
| 3,953,057 A | * | 4/1976 | Petzetakis ....................... 285/67 |
| 4,019,512 A | * | 4/1977 | Tenczar ......................... 604/905 |
| 4,137,930 A | * | 2/1979 | Scholle ............................. 285/4 |
| 4,187,846 A | * | 2/1980 | Lolachi et al. ................ 604/905 |
| 4,247,133 A | * | 1/1981 | Moller .............................. 285/4 |
| 4,253,684 A | | 3/1981 | Tolbert et al. |
| 4,265,280 A | | 5/1981 | Ammann et al. |
| 4,306,705 A | * | 12/1981 | Svensson ...................... 604/905 |
| 4,338,933 A | * | 7/1982 | Bayard et al. ................. 604/905 |

(Continued)

FOREIGN PATENT DOCUMENTS
JP    29-8626 B    10/1952
(Continued)

*Primary Examiner* — David E Bochna
(74) *Attorney, Agent, or Firm* — Dickstein Shapiro LLP (57) ABSTRACT

A method and a device are provided for interconnecting, sealed against contamination, the ends of tubes by two cooperating connecting components, each having an inlet and an outlet for connection to each other. The connecting components each have a connecting plane, into which the outlets open, each covered by a protective component, and which are movable into engagement with each other with the outlets facing each other. A locking element, which is slidably arranged on one connecting component, is, in a controlled manner and without interruption of the sliding movement, movable onto the other connecting component to a distinct end position. The protective components are removable by means of the locking element when this is moved, and the outlets are sealingly pressable against each other. The locking element is prevented from moving until a predetermined force is applied in the moving direction.

14 Claims, 4 Drawing Sheets

U.S. PATENT DOCUMENTS

| | | | |
|---|---|---|---|
| 4,418,945 A | | 12/1983 | Kellogg |
| 4,439,193 A | * | 3/1984 | Larkin .......................... 604/905 |
| RE32,056 E | | 12/1985 | Granzow et al. |
| 4,576,199 A | * | 3/1986 | Svensson et al. ............. 604/905 |
| 4,630,630 A | | 12/1986 | Reynolds et al. |
| 4,815,884 A | * | 3/1989 | Halliday et al. ................... 285/4 |
| 4,844,513 A | * | 7/1989 | St. Louis et al. .................. 285/4 |
| 4,935,010 A | * | 6/1990 | Cox et al. ....................... 604/905 |
| 5,078,429 A | * | 1/1992 | Braut et al. ........................ 285/4 |
| 5,106,127 A | * | 4/1992 | Briet ................................ 285/4 |
| 5,393,101 A | | 2/1995 | Matkovich |
| 5,810,398 A | | 9/1998 | Matkovich |
| 5,980,506 A | * | 11/1999 | Mathiasen .................... 604/905 |
| 6,077,259 A | * | 6/2000 | Caizza et al. ................. 604/905 |
| 6,481,756 B1 | * | 11/2002 | Field et al. .................... 604/905 |
| 7,137,974 B2 | * | 11/2006 | Almasian et al. ............. 604/905 |
| 7,396,051 B2 | * | 7/2008 | Baldwin et al. ............... 604/905 |

FOREIGN PATENT DOCUMENTS

| | | |
|---|---|---|
| JP | 49-129223 A | 12/1974 |
| JP | 57-204393 A | 12/1982 |
| JP | 8-502339 A | 3/1996 |

* cited by examiner

METHOD AND DEVICE FOR INTERCONNECTING, SEALED AGAINST CONTAMINATION, THE ENDS OF ELONGATE ELEMENTS SUCH AS TUBES OR PIPES

FIELD OF THE INVENTION

The present invention relates generally to a connecting method and a connecting device preferably of the disposable type to be used in a variety of fields, for instance the pharmaceutical, food and biotechnology fields, and also in other contexts such as handling of pharmaceutical preparations on patients, blood handling, handling of cytostatics, where the safety of the operator is important, handling of fluids in the semiconductor and aerospace industry etc.

More specifically, the invention relates to a method of interconnecting, sealed against contamination and/or in a sterile manner, the ends of elongate elements such as tubes or pipes by at least two cooperating connecting means each having an inlet for the associated end and each having an outlet for connection to each other, each connecting means having a connecting plane, into which the outlet opens, covered by a protective means.

The invention also relates to a device for interconnecting, sealed against contamination and/or in a sterile manner, the ends of elongate elements such as tubes or pipes by at least two cooperating connecting means each having an inlet for the associated end and each having an outlet for connection to each other, the connecting means being provided with connecting planes, into which the outlet opens, covered by a protective means.

BACKGROUND ART

In many fields and contexts, of which a few have been mentioned above as examples, it is normally necessary to transfer a fluid, such as a more or less thin fluid or a gas or a mixture thereof, from one place, such as a process or storage unit, for instance a vessel or bag of a conventional type or of a now more common disposable type or other equipment, to another place, without the fluid risking to be contaminated with foreign particles, especially airborne bacteria and the like or gaseous air pollutants.

In the fields/contexts above, there is, inter alia, a more or less continuous need for sampling of fluids, for instance for microbiological control, cell counting and other chemical analyses, or supply of regulating or active substances, such as a pH buffer or a biological starter culture, in certain process steps in the manufacture of products in the respective fields.

Whenever a new connection for the above purposes has to be made to transfer the fluid from one place to another, there is, especially in non-sterile environments, a great risk of contamination of the fluid.

Such connection can occur by introducing a sterile needle, which is connected to one vessel via a tube or pipe, into a sterile membrane connected to the other vessel. In the connecting operation, the connecting components and/or the fluid are exposed to the risk of being contaminated with airborne bacteria, spores etc. and by incorrect handling of the connecting components.

To reduce the risk of contamination when interconnecting two or more process or storage units for transfer of a fluid between them, there has been suggested, instead of the above-described needle connecting device, inter alia according to U.S. Pat. No. 3,909,910 a sterile connector for interconnecting the ends of elongate elements such as tubes or pipes by at least two cooperating connecting means each having an inlet for the associated end and an outlet for connection to each other. The connector has sealing means, which are arranged on the connecting means around the outlets and are provided with protective means in the form of thin films or foils which cover the sealing means and the outlets and are removable in the final interconnection. With the connecting means arranged end-to-end against each other with the outlets opposite each other and with the sealing means pressed against each other, by means of, for instance, a spring-loaded clamp, under elastic deformation, the protective means engaging each other are manually pulled off at the same time from the connecting means.

When pulling off the protective means, they are folded back upon themselves, and even if they are very thin there occurs in the folding area a small gap with a width corresponding to the width of the protective means. This gap "moves" in the pull-off direction and passes the area of the outlets in the sealing means and the connecting means, so that airborne contamination is entrained by the gap and risks entering the outlets and contaminating the fluid.

OBJECTS OF THE INVENTION

The main object of the present invention is to provide a method and a device of the type stated by way of introduction, which in a new and unique manner effectively eliminate the above-described drawbacks and the risks of contamination of fluids when interconnecting two or more vessels or process units for transfer of fluid between them.

Another object of the invention is to provide such a method and a device which ensure an interconnection, sealed against contamination, in such a manner that airborne bacteria, spores, microorganisms and other external contaminants cannot enter and mix with the fluids that are transferred between the connecting means.

A further object of the invention is to provide a method and a device where all conventional requirements are satisfied as to contamination-free transfer of the fluid all the way from one process unit/vessel to another and/or to supply of substances or sampling etc.

SUMMARY OF THE INVENTION

The above and other related objects are achieved in a simple as well as effective manner in the method according to the invention by the connecting planes of the connecting means being moved into engagement with each other with the outlets facing each other, and a locking element slidably arranged on one connecting means being, in a controlled manner and without interruption of the sliding movement, moved at least partially onto the other connecting means to a distinct end position, while at the same time the protective means covering the outlets are removed by the locking element when this is moved and while at the same time the outlets are sealingly pressed against each other.

Regarding the device according to the invention, the above and other related objects are achieved in the same simple and effective manner by the connecting planes being movable to engage each other with the outlets facing each other, and a locking element slidably arranged on one connecting means being, in a controlled manner and without interruption of the sliding movement, movable at least partially onto the other connecting means to a distinct end position, while at the same time the protective means covering the outlets are removable by the locking element when this is moved and while at the same time the outlets are sealingly pressable against each other.

In a preferred embodiment of the method, the locking element is prevented from moving until a predetermined force is applied in the moving direction, after which a catch releases and the locking element is quickly moved to the distinct end position.

In this context it is convenient if the locking element is locked in the distinct end position for permanent and irreversible interconnection of the connecting means.

In addition, in a particularly preferred embodiment, the connecting planes are provided with sealing means around the outlets, on which sealing means the protective means are arranged and which are pressed against each other when removing the protective means.

Correspondingly, in the device according to the invention, the connecting planes suitably have sealing means around the outlets, on which sealing means the protective means are arranged and which are pressable against each other when removing the protective means.

In a particularly preferred further development of the device according to the invention, the connecting planes extend substantially in the longitudinal direction of the associated connecting means, the connecting means preferably being connected to each other by means of hinges and being pivotable towards each other to move the connecting planes into engagement with each other.

Moreover it is particularly convenient if the connecting means, for protection of the protective means against contact and contamination and for protection against overpressure and underpressure in the connecting means, are each provided with a protective element over the respective protective means, which protective elements are removed before the connecting planes are moved into engagement with each other.

BRIEF DESCRIPTION OF THE DRAWINGS

The invention will now be described in more detail with reference to the accompanying drawings, in which.

DESCRIPTION OF A PREFERRED EMBODIMENT

The accompanying drawings illustrate a sterile connector generally designated 1, made of a suitable material such as plastic for connection, sealed against contamination, of two or more process units (not shown), such as receptacles/vessels of metal or rigid plastic or bags of non-rigid plastic of a conventional re-use type or of a disposable type, via such elongate elements as tubes 2 or pipes preferably made of non-rigid plastic.

More specifically, the sterile connector 1 comprises as main components first and second connector halves 3, 4, also referred to as male and female parts. The connector halves 3, 4 each have an elongate connecting means 5 and 6 respectively, which at their outer free ends each have an inlet 7 for connecting one end of the tubes 2. The other ends of the tubes 2 are, in a manner not shown in detail, connected to the associated process unit. As a variant, one of the connecting means 5, 6 can at its free end be directly connected to its process unit.

Each connecting means 5, 6 has an elongate through duct 8 which extends from the associated inlet 7 to an outlet 9 towards the other ends of the connecting means 5, 6. The outlets 9 open into substantially flat connecting planes 10 on one side of the connecting means 5, 6 and extend substantially in the longitudinal direction thereof. When interconnecting the two connecting means 5, 6 in a manner that will be described below, the connecting planes 10 of the connecting means are movable into engagement with each other with the outlets 9 facing each other and positioned opposite each other in order to allow, after the interconnection, contamination-free transfer of a fluid (not shown), such as a gas or liquid or a mixture thereof, between them and thus the process units.

Sealing means 11, 12 for contamination-free sealing between the two interconnectable connecting means 5, 6 are each arranged on a connecting plane 10 of the connecting means around the associated outlet therein. The sealing means 11, 12 are each provided with a protective means in the form of a protective film 13 of a very thin and yet very tight plastic. The protective films 13 cover the associated sealing means 11, 12 and outlets 9 and are adapted to be removed in conjunction with the final interconnection of the connecting means 5, 6.

At least the sealing means 12 arranged on the connecting means 6 of the second connector half 4, the female part, has the form of an insert 14 arranged in the connecting means and made of an elastically yieldable material such as plastic, rubber or the like, with elastic and sealing properties that are necessary for the purpose.

In the embodiment illustrated, a further, substantially circumferential seal 15 is arranged outside and around each sealing means 11, 12, which seal is also made of a suitable, elastically yieldable material such as plastic or rubber and is arranged on the associated connecting means 5, 6. The above-described protective films 13 are at their outer edge, that is along their periphery, attached to the seals 15 in a sealing but tear-off manner, for instance by gluing, welding or the like. In a manner that will be described below, the seals 15 are movable, interleaved with the protective films 13, into engagement with each other when interconnecting the connecting means 5, 6.

The sealing means 11, 12 of the connecting means 5, 6 are each provided with at least one recess 16 and 17 respectively, which has the form of a groove or depression and extends wholly or partly around the associated outlet 9 in the connecting means 5, 6. The recesses 16, 17 receive or contain a gas, for instance an inert gas or a sterile gas, such as sterile air.

In the embodiment illustrated in the drawings, the sealing means 11, 12 are provided with two groups of recesses 16, 17 with different volumes, positioned one outside the other and cooperating in pairs. However, there is nothing to prevent that there is only one recess 16, 17 or three or more recesses 16, 17 positioned one outside the other around the associated outlet 9.

When interconnecting the connecting means 5, 6, the sealing means 11, 12 are in the same way as the seals 15 movable into engagement with each other, interleaved with the protective films 13. When the connecting means 5, 6 are pressed against each other, the volume or the different volumes of the recesses 16, 17 is/are reduced, depending on the number of groups of recesses, thus increasing the pressure of the gas therein evenly or differently for the same reasons.

When after that the protective films 13 are, in a manner described below, removed or torn off simultaneously and jointly from the sealing means 11, 12 and the seals 15, the pressure increase in the recesses 16, 17 forces the gas out of the recesses, thus preventing penetration of contamination into the outlets 9 of the connecting means 5, 6 in the final interconnection of the same.

In the embodiment illustrated, in which two or more groups of recesses 16, 17 one outside the other are arranged and where the highest gas pressure prevails in the innermost group and a successively decreasing gas pressure prevails in the group or the groups outside the same, the gas is forced, when removing the protective films 13, out of the group with the highest pressure to the group or groups with a lower pressure outwards to the environment 18.

On the connecting means 6 of the second connector half 4, the female part, a sleeve-shaped locking element 23 is longitudinally guided in guides 27 on opposite sides of the connecting means 6. It is most important for the locking element 23, in a controlled manner and without interruption of the sliding movement in the direction of arrow A, see FIG. 12, to be quickly slidable a distance onto and around the connecting means 5 of the first connector half 3 to a distinct end position 24.

Figure 12:
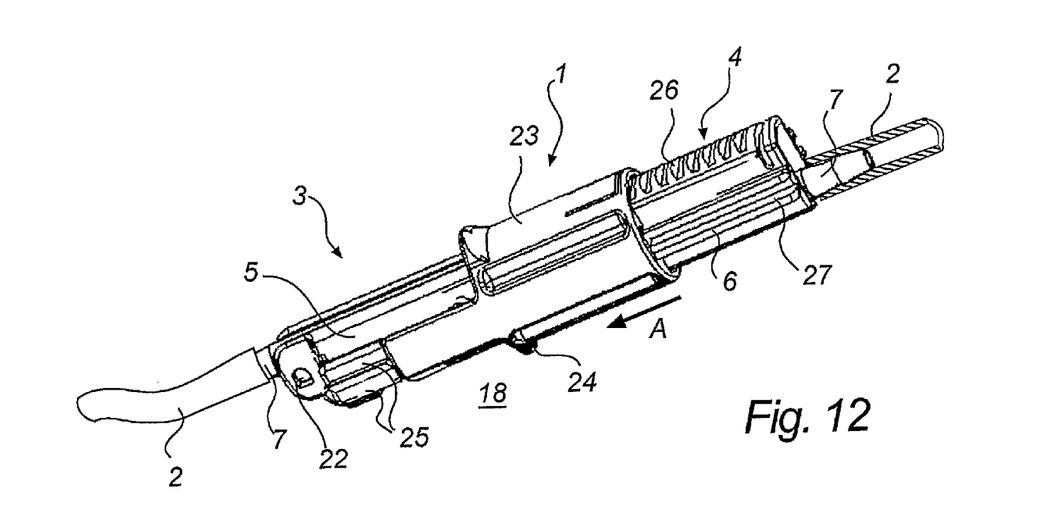

To this end, the locking element 23 is, by a catch 26, here in the form of a snap lock between the locking element and the connecting means 6, prevented from sliding, until a fairly great predetermined force is applied, manually or in some other manner, in the direction of arrow A. With this force applied, the catch 26 distinctly releases and the locking element 23 is very quickly movable to the distinct end position 24.

Simultaneously with this sliding movement of the locking element 23, the protective films 13 covering the sealing means 11, 12 and the outlets 9 are removed by means of the locking element by being entrained by this via drivers 25, while at the same time the outlets 9 are sealingly pressable against each other.

By the quick sliding movement of the locking means 23 to the distinct end position 24, the protective films are also quickly entrained and removed, thus preventing penetration of contamination into the outlets 9 in the final interconnection of the connector halves 3, 4 of the sterile connector 1.

To secure the interconnection by providing a permanent and irreversible interconnection of the connecting means 5, 6 and thus prevent unintentional opening of the sterile connector, the locking element 23 is in the shown embodiment lockable in the distinct end position 24 by a tamper-proof locking means (not shown).

The above-mentioned connecting planes 10 extend in the preferred embodiment substantially in the longitudinal direction of the associated connecting means 5, 6, that is substantially parallel to the longitudinal axis thereof. The connecting means 5, 6 are connectable to each other at their one end by means of a hinge-like snap joint 22 so that they are pivotable towards each other to move the connecting planes 10 into engagement with each other.

In order to protect, before the interconnection and before the connecting planes 10 in the manner described above are moved into engagement with each other, the protective films 13 against contact and contamination and/or in order to protect the connecting means 5, 6 against overpressure and underpressure, especially in the area of the inlets and outlets 7, 9 and the ducts 8, the connecting means 5, 6 are each provided with a lid-shaped protective element 19 over the respective sealing means 11, 12 and the associated protective film 13. The protective elements 19 are then removable before the connecting planes are moved into engagement with each other. The removal can easily occur by means of an opener 20 with an integrated pull ring 21.

The function and handling of the above-described sterile connector 1 will now be briefly described in different steps with special reference to FIGS. 7-12.

Figure 1:
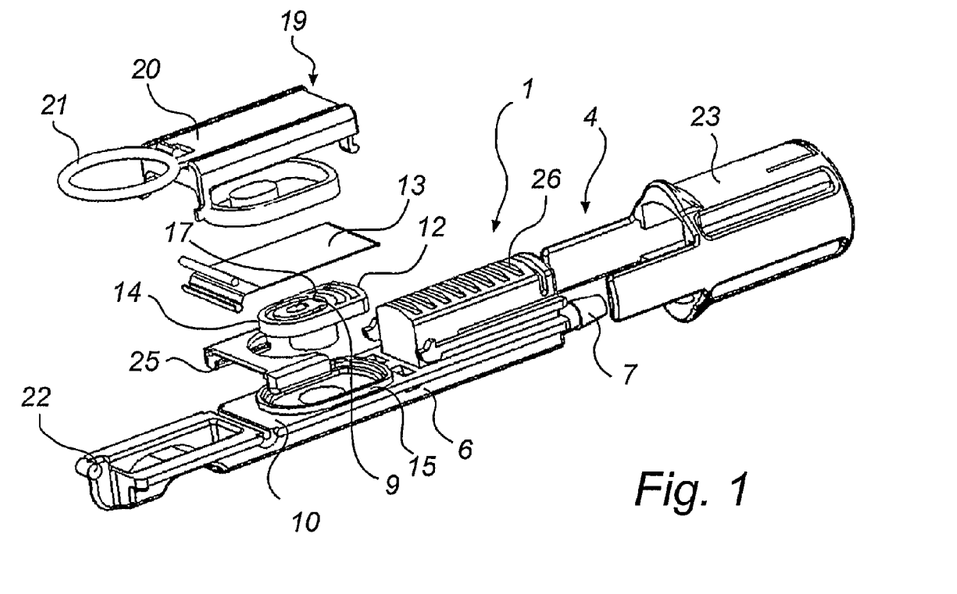
FIG. 1 is an exploded side view, in oblique perspective, of a first connector half included in a sterile connector.
Figure 2:
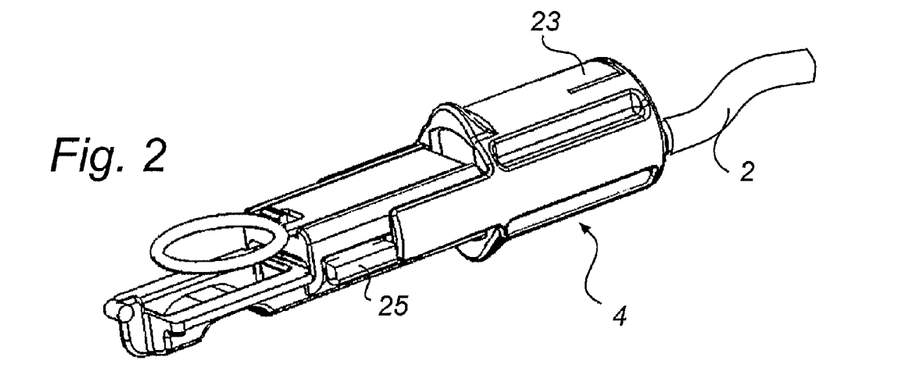
FIG. 2 illustrates in the same perspective the connector half according to FIG. 1 in the assembled state.
Figure 3:
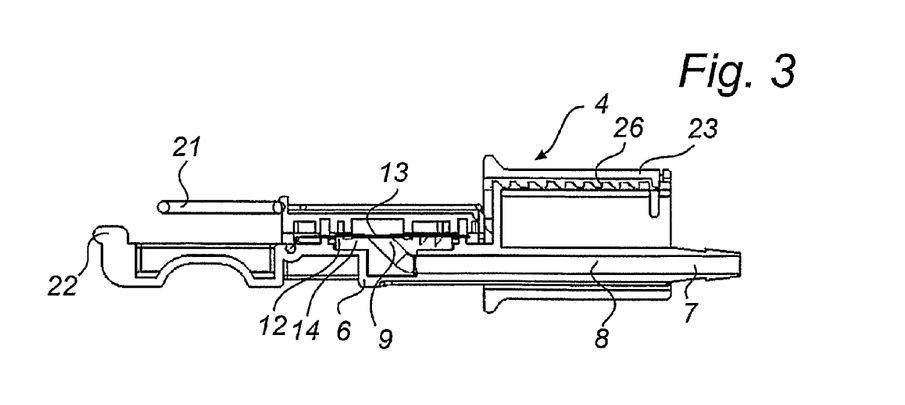
FIG. 3 is a central longitudinal section of the connector half according to FIG. 2.
Figure 4:
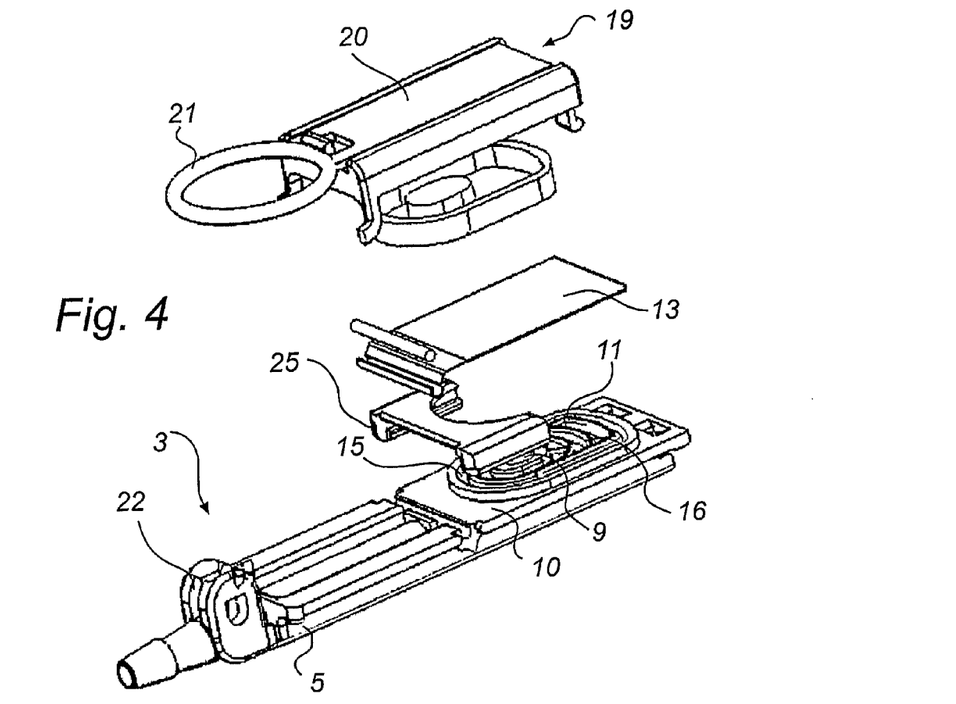
FIG. 4 is an exploded side view, in oblique perspective corresponding to FIG. 1, of a second connector half included in the sterile connector.
Figure 5:
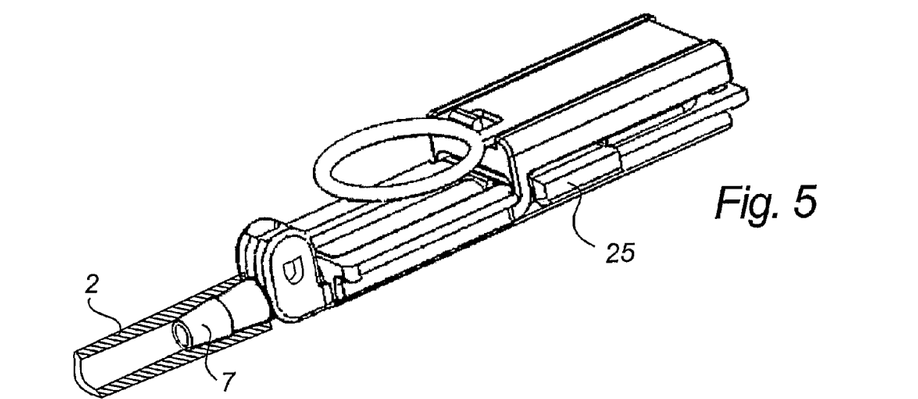
FIG. 5 illustrates in the same perspective as FIG. 4 the second connector half in the assembled state.
Figure 6:
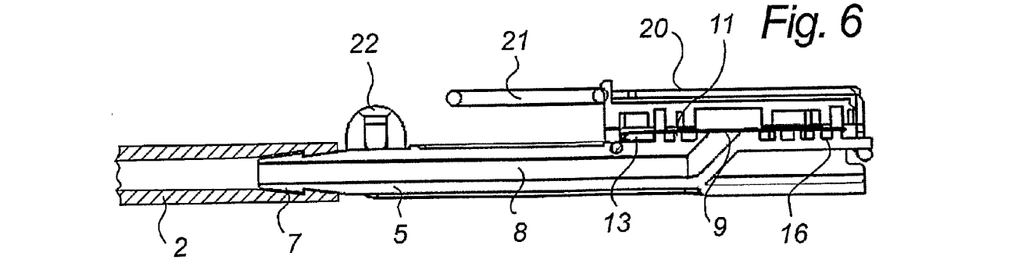
FIG. 6 is a central longitudinal section of the connector half according to FIG. 5, and FIGS. 7-12 illustrate slightly schematically in an oblique side view in perspective successive steps for interconnecting the sterile connector according to FIGS. 1-6 to be ready for use.
Figure 7:
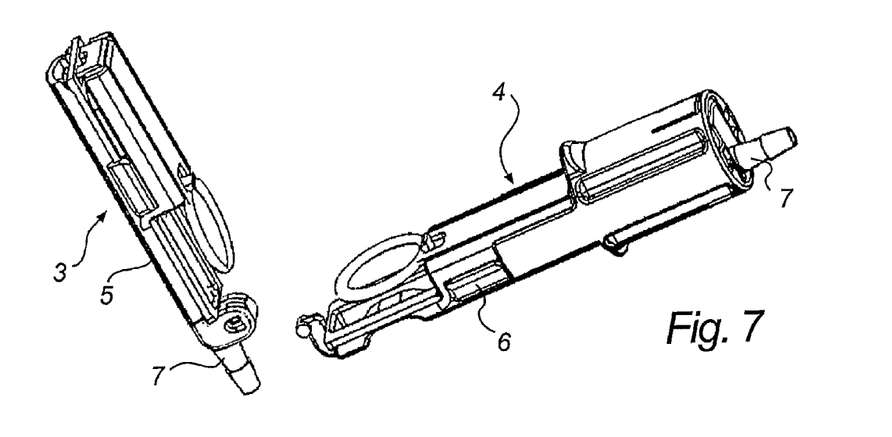

FIG. 7 shows step 1, the starting position, where the connector halves 3, 4 of the sterile connector 1 have been removed separately from their respective sterile transport and storage packages (not shown) and where the connecting tubes 2 are connected to the respective inlets 7.

Figure 8:
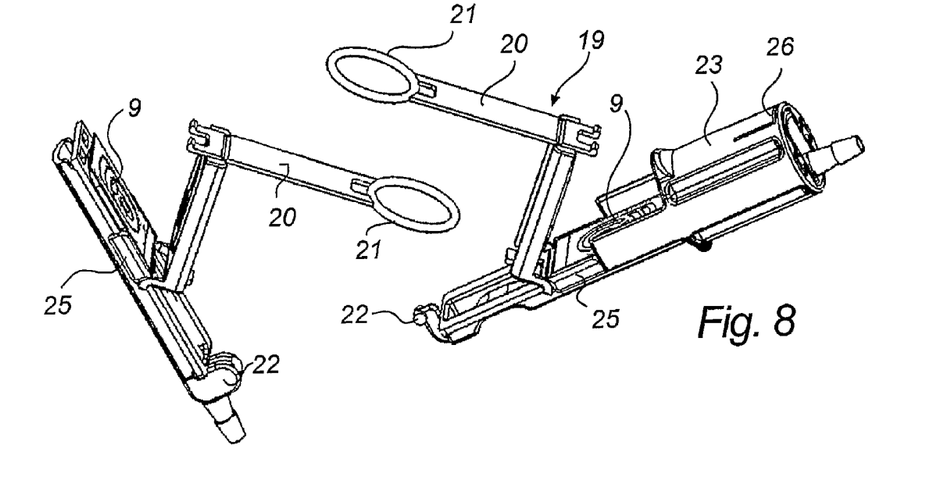
Figure 9:
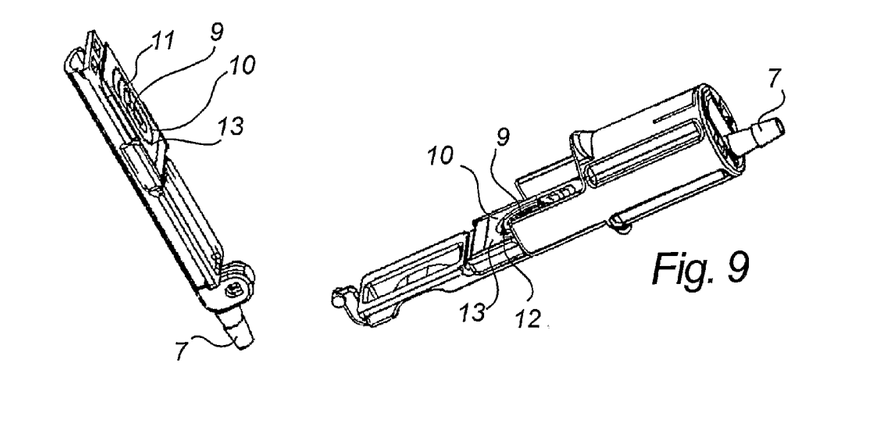

In step 2, see FIG. 8, the lid-shaped protective elements 19 over the sealing means 11, 12 on the connecting means 5, 6 of the connector halves 3, 4 are removed by means of the opener 20 with its pull ring 21. Step 3 in FIG. 9 has now been reached.

Figure 10:
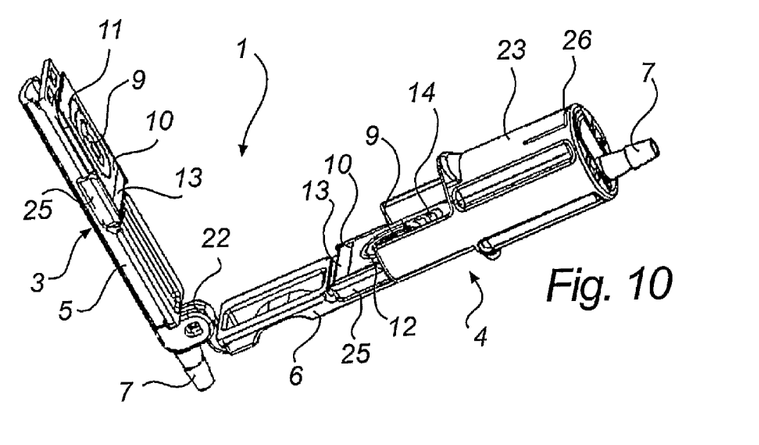

Step 4 is shown in FIG. 10, where the connector halves 3, 4 are articulated to each other by the hinge 22 by snap action.

Figure 11:
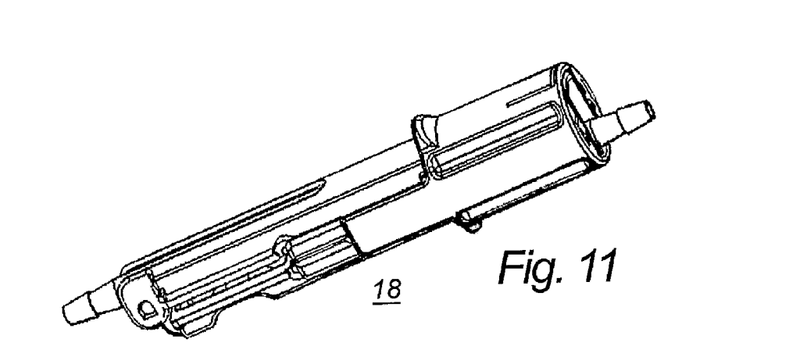

FIG. 11 illustrates step 5, where the connecting planes 10 of the connecting means 5, 6 of the connector halves 3, 4 are moved into engagement with each other by pivoting the connector halves towards each other via the hinge 22 until the first connector half 3 with its outer free end snaps under the sleeve-shaped locking element 23 which is longitudinally guided on the second connector half 4.

In step 6, the final position, shown in FIG. 12, the final interconnection of the connector halves 3, 4 and their components is provided by the locking element 23 being moved, in the manner described above, onto the first connector half 3 to the distinct end position 24. At the same time the protective films 13 covering the sealing means 11, 12 and the outlets 9 of the connecting means 5, 6 are removed via the drivers 25 by the locking element 23 when this is moved and the sealing means and, thus, the outlets 9 are pressed against each other, sealed against contamination.

It goes without saying that the invention should not be considered limited to the embodiment described above and illustrated in the drawings, with its conceivable variants and alternatives, but can be modified in various ways within the scope of that stated in the appended claims.

The invention claimed is:

1. A method of interconnecting, sealed against contamination, the ends of elongate elements such as tubes or pipes by at least two cooperating connecting means each having an inlet for an associated end and each having an outlet for connection to each other, each connecting means having a connecting plane, into which the outlet opens, covered by a protective film, the method comprising:

moving into engagement the connecting planes of the connecting means with the outlets facing each other; and moving a locking element, slidably arranged on one connecting means, in a controlled manner and without interruption of the sliding movement, at least partially onto the other connecting means to a distinct end position, while at the same time the protective film covering the outlets are removed by the locking element when it is moved and while at the same time the outlets are sealingly pressed against each other.

2. A method as claimed in claim 1, wherein the locking element is prevented from moving until a predetermined force is applied in the moving direction, after which a catch releases and the locking element is quickly moved to the distinct end position.

3. A method as claimed in claim 1, wherein the locking element is locked in the distinct end position for permanent and irreversible interconnection of the connecting means.

4. A method as claimed in claim 1, wherein the connecting means, for protection of the protective film against contact and contamination and for protection against overpressure and underpressure in the connecting means, are each provided with a protective element over the associated protective film, which protective elements are removed before the connecting planes are moved into engagement with each other.

5. A method of interconnecting, sealed against contamination, the ends of elongate elements such as tubes or pipes by at least two cooperating connecting means each having an inlet for an associated end and each having an outlet for connection to each other, each connecting means having a connecting plane, into which the outlet opens, covered by a protective means, the method comprising:
    moving into engagement the connecting planes of the connecting means with the outlets facing each other; and
    moving a locking element, slidably arranged on one connecting means, in a controlled manner and without interruption of the sliding movement, at least partially onto the other connecting means to a distinct end position, while at the same time the protective means covering the outlets are removed by the locking element when it is moved and while at the same time the outlets are sealingly pressed against each other,
    wherein the connecting planes are provided with sealing means around the outlets, on which sealing means the protective means are arranged and which are pressed against each other when the protective means are removed.

6. A method of interconnecting, sealed against contamination, the ends of elongate elements such as tubes or pipes by at least two cooperating connecting means each having an inlet for an associated end and each having an outlet for connection to each other, each connecting means having a connecting plane, into which the outlet opens, covered by a protective means, the method comprising:
    moving into engagement the connecting planes of the connecting means with the outlets facing each other; and
    moving a locking element, slidably arranged on one connecting means, in a controlled manner and without interruption of the sliding movement, at least partially onto the other connecting means to a distinct end position, while at the same time the protective means covering the outlets are removed by the locking element when it is moved and while at the same time the outlets are sealingly pressed against each other,
    wherein the connecting planes are given an extent substantially in the longitudinal direction of the associated connecting means and in which the connecting means are hingedly connected to each other and pivoted towards each other to make the connecting planes engage each other.

7. A device for interconnecting, sealed against contamination, the ends of elongate elements such as tubes or pipes by at least two cooperating connecting means each having an inlet for an associated end and each having an outlet for connection to each other, each connecting means being provided with a connecting plane into which the outlet opens, covered by a protective film, the device comprising:
    connecting planes movable to engage each other with the outlets facing each other; and
    a locking element slidably arranged on one connecting means, the locking element being movable, in a controlled manner and without interruption of the sliding movement, at least partially onto the other connecting means to a distinct end position, while at the same time the protective film covering the outlets are removable by the locking element when it is moved and while at the same time the outlets are sealingly pressable against each other.

8. A device as claimed in claim 7, in which the locking element is prevented from moving until a predetermined force is applied in the moving direction, after which a catch is made to release and the locking element is quickly movable to the distinct end position.

9. A device as claimed in claim 7, in which the locking element is lockable in the end position for permanent and irreversible interconnection of the connecting means.

10. A device as claimed in claim 7, in which the connecting means, for protection of the protective film against contact and contamination and for protection against overpressure and underpressure in the connecting means, are each provided with a protective element over the respective protective film, which protective elements are removable before the connecting planes are movable into engagement with each other.

11. A device for interconnecting, sealed against contamination, the ends of elongate elements such as tubes or pipes by at least two cooperating connecting means each having an inlet for an associated end and each having an outlet for connection to each other, each connecting means being provided with a connecting plane into which the outlet opens, covered by a protective means, the device comprising:
    connecting planes movable to engage each other with the outlets facing each other the connecting planes having sealing means around the outlets, on which sealing means the protective means are arranged and which are pressable against each other when removing the protective means; and
    a locking element slidably arranged on one connecting means, the locking element being movable, in a controlled manner and without interruption of the sliding movement, at least partially onto the other connecting means to a distinct end position, while at the same time the protective means covering the outlets are removable by the locking element when it is moved and while at the same time the outlets are sealingly pressable against each other.

12. A device for interconnecting, sealed against contamination, the ends of elongate elements such as tubes or pipes by at least two cooperating connecting means each having an inlet for an associated end and each having an outlet for connection to each other, each connecting means being provided with a connecting plane into which the outlet opens, covered by a protective means, the device comprising:
    connecting planes movable to engage each other with the outlets facing each other wherein the connecting planes extend substantially in the longitudinal direction of the associated connecting means and wherein the connecting means are connected to each other by means of a hinge and are pivotable towards each other to move the connecting planes into engagement with each other; and
    a locking element slidably arranged on one connecting means, the locking element being movable, in a controlled manner and without interruption of the sliding movement, at least partially onto the other connecting means to a distinct end position, while at the same time the protective means covering the outlets are removable by the locking element when it is moved and while at the same time the outlets are sealingly pressable against each other.

13. A method of interconnecting, sealed against contamination, the ends of elongate elements such as tubes or pipes by at least two cooperating connecting means each having an inlet for an associated end and each having an outlet for connection to each other, each connecting means having a connecting plane, into which the outlet opens, covered by a protective means, the method comprising:
 simultaneously placing the protective means in contact with each other and moving the connecting planes of the connecting means into engagement with the outlets facing each other; and
 moving a locking element, slidably arranged on one connecting means, in a controlled manner and without interruption of the sliding movement, at least partially onto the other connecting means to a distinct end position, while at the same time the protective means covering the outlets are removed by the locking element when it is moved and while at the same time the outlets are sealingly pressed against each other.

14. A device for interconnecting, sealed against contamination, the ends of elongate elements such as tubes or pipes by at least two cooperating connecting means each having an inlet for an associated end and each having an outlet for connection to each other, each connecting means being provided with a connecting plane into which the outlet opens, covered by a protective means, the device comprising:
 connecting planes movable to engage each other with the outlets facing each other, and to simultaneously place the protective means in contact with each other; and
 a locking element slidably arranged on one connecting means, the locking element being movable, in a controlled manner and without interruption of the sliding movement, at least partially onto the other connecting means to a distinct end position, while at the same time the protective means covering the outlets are removable by the locking element when it is moved and while at the same time the outlets are sealingly pressable against each other.

\* \* \* \* \*